(12) United States Patent
Lee et al.

(10) Patent No.: US 11,154,568 B2
(45) Date of Patent: Oct. 26, 2021

(54) COMPOSITION FOR RELIEVING HANGOVER OR COMPOSITION FOR PREVENTING, ALLEVIATING OR TREATING ALCOHOLIC LIVER DISEASE, COMPRISING B-GLUCAN AS ACTIVE INGREDIENT

(71) Applicant: QUEGEN BIOTECH CO., LTD., Siheung-si (KR)

(72) Inventors: Jong Dae Lee, Seoul (KR); Sung Hong Kim, Seoul (KR); Young Kyun Kim, Bhcheon-si (KR); Je Kyoung Kim, Bucheon-si (KR); Yong Man Jang, Siheung-si (KR); Min Ji Kim, Donghae-si (KR); Eun Ji Park, Gwangju (KR); Chul Su Yang, Ansan-si (KR)

(73) Assignee: QUEGEN BIOTECH CO., LTD., Siheung-si (KR)

( * ) Notice: Subject to any disclaimer, the term of this patent is extended or adjusted under 35 U.S.C. 154(b) by 0 days.

(21) Appl. No.: 16/646,854

(22) PCT Filed: Aug. 29, 2018

(86) PCT No.: PCT/KR2018/009974
§ 371 (c)(1),
(2) Date: Mar. 12, 2020

(87) PCT Pub. No.: WO2019/059549
PCT Pub. Date: Mar. 28, 2019

(65) Prior Publication Data
US 2021/0008094 A1 Jan. 14, 2021

(30) Foreign Application Priority Data

Sep. 19, 2017 (KR) .................. 10-2017-0120339
Aug. 28, 2018 (KR) .................. 10-2018-0101390

(51) Int. Cl.
| | | |
|---|---|---|
| A61K 31/716 | (2006.01) | |
| A23L 2/52 | (2006.01) | |
| A23L 31/00 | (2016.01) | |
| A23L 33/00 | (2016.01) | |
| A23L 33/125 | (2016.01) | |
| A61P 1/16 | (2006.01) | |
| A61P 25/32 | (2006.01) | |

(52) U.S. Cl.
CPC .............. *A61K 31/716* (2013.01); *A23L 2/52* (2013.01); *A23L 31/00* (2016.08); *A23L 33/125* (2016.08); *A23L 33/40* (2016.08); *A61P 1/16* (2018.01); *A61P 25/32* (2018.01); *A23V 2002/00* (2013.01)

(58) Field of Classification Search
CPC .......... A61K 31/716; A61P 25/32; A61P 1/16; A23L 31/00; A23L 33/40; A23L 2/52; A23L 33/125; A23V 2002/00
USPC ......................................................... 514/54
See application file for complete search history.

(56) References Cited

FOREIGN PATENT DOCUMENTS

| | | |
|---|---|---|
| JP | 4975947 | 7/2012 |
| KR | 20040001827 | 1/2004 |
| KR | 100707917 | 4/2007 |
| KR | 100892355 | 4/2009 |
| KR | 100909857 | 7/2009 |
| KR | 20130118058 | 10/2013 |
| KR | 20180042936 | 4/2018 |
| WO | WO 2017/011523 | * 1/2017 |

OTHER PUBLICATIONS

Glossary of medical education terms, Institute of International Medical Education. http://www.iime.org/glossary.htm Accessed in Mar. 2013. (Year: 2013).*
Sun et al. Therapeutic manipulation of gut microbiota by polysaccharides of Wolfi poria cocos reveals the contribution of the gut fungi-induced PGE2 to alcoholic hepatic steatosis. Gut Microbes 2020, vol. 12, No. 1, e1830693 (13 pages) (Year: 2020).*
Chihara et al. Antitumour Polysaccharide derived Chemically from Natural Glucan (Pachyman). Nature 225:943-944, 1970. (Year: 1970).*
Du et al. Characterization and Anti-Inflammatory Potential of an Exopolysaccharide from Submerged Mycelial Culture of Schizophyllum. Front. Pharmacol. 8:252, published on May 15, 2017. doi: 10.3389/fphar.2017.00252 (Year: 2017).*
International Search Report and Written Opinion issued in corresponding application No. PCT/KR2018/009974, dated Mar. 11, 2019.
Kim, Gunwoo, "Quegen Biotech Co., Ltd. successfully captured 3 billion investments from institutions, entering the field of health functional foods+pharmaceuticals" *Money Today*, 2016, Retrieved from the Internet: <URL:http://m.mtco.kr/renew/view.html?no~2016082411045844882>.

* cited by examiner

*Primary Examiner* — Yih-Horng Shiao
(74) *Attorney, Agent, or Firm* — Norton Rose Fulbright US LLP (57) ABSTRACT

The present invention relates to a composition for relieving a hangover or a composition for preventing, alleviating or treating alcoholic liver disease, comprising a β-glucan as an active ingredient.

2 Claims, 4 Drawing Sheets

ADH, ALDH activity measured in serum (T1=5 min; T2=60 min), showing activity (mU) per mL of tested sample, background signal subtracted.

Body weight and tissue weight in each group of mice (*n*=5)

At 6 wks

| | EXPERIMENTAL GROUP 1 | COMPARATIVE EXPERIMENTAL GROUP 1 | COMPARATIVE EXPERIMENTAL GROUP 2 | COMPARATIVE EXPERIMENTAL GROUP 3 |
|---|---|---|---|---|
| Initial body weight (g) | 18.5±0.53 | 18.42±0.48 | 18.79±0.37 | 18.46±0.44 |
| Final body weight (g) | 21.94±0.34 | 24.16±0.58** | 21.9±0.65 | 22.51±0.56 |
| Liver weight (g) | 1±0.53 | 1.37±0.31* | 0.99±0.47 | 0.81±0.28 |

$p^* < 0.05$, $p^{**} < 0.01$ compare with Vehicle.

FIG. 4

Serum chemistry in each group of mice (*n*=5)

At 6 wks

| | EXPERIMENTAL GROUP 1 | COMPARATIVE EXPERIMENTAL GROUP 1 | COMPARATIVE EXPERIMENTAL GROUP 2 | COMPARATIVE EXPERIMENTAL GROUP 3 |
|---|---|---|---|---|
| Triglyceride (mg/dL) | 77.1±3.81 | 82.19±3.18 | 78.14±3.97 | 80.14±0.01 |
| Total cholesterol (mg/dL) | 39.27±0.4 | 65.06±12.00** | 40.61±0.77 | 34.27±11.85 |
| HDL (mg/dL) | 17.23±2.48 | 17.8±1.93 | 17.14±2.72 | 17.94±1.95 |
| LDL (mg/dL) | 9.63±1.59 | 9.97±0.85 | 10.53±0.39 | 9.56±0.11 |
| GOT/AST (IU/L) | 14.79±1.73 | 25.15±4.89** | 13.8±1.17 | 14.2±0.07 |
| γ-GPT/ALT (IU/L) | 33.264±1.14 | 74.13±4.01*** | 33.88±1.27 | 33.14±0.03 |

HDL:high-density lipoproteins, LDL: low-density lipoproteins, GOT: glutamic oxaloacetic transaminase/AST, γ-GPT: glutamate-pyruvate Transaminase/ALT p* <0.05, p <0.01, p* <0.001 compare with Vehicle.

COMPOSITION FOR RELIEVING HANGOVER OR COMPOSITION FOR PREVENTING, ALLEVIATING OR TREATING ALCOHOLIC LIVER DISEASE, COMPRISING B-GLUCAN AS ACTIVE INGREDIENT

CROSS-REFERENCE TO RELATED APPLICATIONS

This application is a national phase application under 35 U.S.C. § 371 of International Application No. PCT/KR2018/009974, filed Aug. 29, 2018, which claims priority to and the benefit of Korean Patent Application No. 10-2017-0120339, filed Sep. 19, 2017, and Korean Patent Application No. 10-2018-0101390, filed Aug. 28, 2018. The contents of the referenced patent applications are incorporated into the present application by reference.

FIELD OF THE DISCLOSURE

The present invention relates to a composition for relieving a hangover or a composition for preventing, alleviating or treating alcoholic liver disease, which includes beta-glucan (β-glucan) (particularly, *Schizophyllum commune*-derived β-glucan) as an active ingredient.

DESCRIPTION OF RELATED ART

Drinking is a prevalent lifestyle around the world, and proper alcohol consumption can enrich people's lives by helping people socialize and improve their health. However, excessive drinking can cause nausea, vomiting, thirst, headaches and muscle pain caused by a hangover, which can negatively affect daily lives. In addition, chronic alcohol consumption causes malnutrition by inhibiting in vivo nutrient uptake or metabolism, and liver diseases such as alcoholic fatty liver, hepatitis, cirrhosis, etc., cancer, diabetes, cardiovascular diseases, and neuropsychiatric disorders, etc., resulting in huge socioeconomic loss. Moreover, chronic alcohol metabolism leads to hypoglycemia and a low body weight, resulting in an energy metabolic imbalance.

When humans drink alcohol, the human body absorbs and breaks down the alcohol. This is called alcohol metabolism, and most of the alcohol absorbed in the body is processed in the liver to be oxidized into acetaldehyde, which is oxidized again to acetic acid. Acetic acid is oxidized into carbon dioxide ($CO_2$) and water ($H_2O$). There are two enzymes involved in alcohol metabolism, such as alcohol dehydrogenase (ADH) and aldehyde dehydrogenase (ALDH). When alcohol is absorbed in the body, a hangover and alcoholic side effects occur. A hangover is a phenomenon in which various side effects such as fatigue, sleep disorders, palpitations, tremors and vomiting occur after drinking, and the main cause of this phenomenon is acetaldehyde accumulated in the body. Acetaldehyde is produced from alcohol absorbed in the body and metabolized by the liver, and is toxic in vivo. Acetaldehyde directly damages liver cells, and causes various side effects as traveling in the body through blood vessels. People who are flushed from drinking have no or a lack of enzymes breaking down acetaldehyde, and such phenomenon is due to the fact that accumulated acetaldehyde makes blood vessels expand and leads to a red face and a shortness of breath. In addition, a certain amount or more of alcohol that can be broken down by the liver is delivered to the brain via the blood, affecting the brain functionality, stimulating the central nervous system and thus reducing judgment. In addition, if acetic acid produced by alcohol metabolism is not broken down into carbon dioxide and water, fat is excessively accumulated in live tissue due to overproduction of fatty acids, leading to alcoholic fatty liver. Accordingly, interest in substances that can eliminate a hangover caused by alcohol consumption and suppresses liver injury is increasing, and studies relating thereto are actively progressing. In the field of alcoholic liver disease, recent advances have generally been made in pathophysiology and the therapeutic area. Liver disease research has been continuously conducted at the laboratory and animal testing levels, and based on the results of these tests, clinical trials are being attempted. In terms of treatment, since introduced in 1971, steroid therapy was the only therapeutic for severe alcoholic hepatitis until 2000. Other than this, many new therapeutics are in clinical trials, and in a recent study in 2014, the effect of *Hovenia dulcis* berry extracts on mitigation of liver injury and weight loss was proven by animal testing.

β-glucans are polysaccharides produced by polymerizing glucose with β-1,3 bonds, and include microorganism-derived β-glucans (β-1,3-glucan or β-1,3-1,6-glucan) produced by being isolated from polysaccharides of the cell walls or cells of microorganisms such as mushrooms, yeasts, etc., and vegetable β-glucan (β-1,3-1,4-glucan) produced by being extracted from cereals such as barley, oats, etc. These glucans may exhibit various physiological activities according to a more specific glucose bond structure, and are high value-added biomaterials used in various ways such as cosmetic additives, dietary supplements, food additives, concrete admixtures and feed additives.

Particularly, β-glucan, for example, in the form of β-(1,6)-branched (1,3)-glucan, known to be present in Schizophyllan of *Schizophyllum commune* has been reported to serve as a natural immune modulator that boosts immunity and does not have resistance and to have physiological activities for anticancer actions and antioxidation. β-glucans are well known as biological response modifiers (BRMs) that act on the human immune system to boost the immunity of the human body, and particularly, it has been reported that β-glucan enhances the overall functions of the immune system by activating the function of macrophages in the immune system, secreting cytokines such as interferons or interleukins, which are proliferation factors of other lymphocytes or leukocytes. In addition, when β-glucans are added to chick feed, they serve as immunomodulators to prevent *Salmonella*. Particularly, as part of improving the efficacy of yeast-derived β-glucan, there were studies of inducing mutations in cell walls by causing artificial mutations in yeast, from the studies, it was found that β-glucans obtained from the mutations exhibit excellent immune and anticancer activities.

SUMMARY OF THE INVENTION

The present invention is directed to providing a pharmaceutical composition for relieving a hangover, which includes β-glucan as an active ingredient.

However, technical problems to be solved in the present invention are not limited to the above-described problems, and other problems which are not described herein will be fully understood by those of ordinary skill in the art from the following descriptions.

The present invention provides a pharmaceutical composition for relieving a hangover, which includes β-glucan as an active ingredient.

The composition may suppress side effects caused by a hangover.

The side effects may be due to a body weight gain, hepatotoxicity or an increase in blood cholesterol level.

The β-glucan may be isolated from *Schizophyllum commune* or a culture thereof.

The β-glucan may have a structure of β-(1,6)-branched (1,3)-glucan.

The β-glucan may be contained at 0.001 to 50 wt % with respect to the total weight of the composition.

According to an exemplary embodiment of the present invention, a pharmaceutical composition for preventing or treating alcoholic liver disease, which includes β-glucan as an active ingredient, is provided.

According to another exemplary embodiment of the present invention, a health functional food for relieving a hangover, which includes β-glucan as an active ingredient, is provided.

According to still another exemplary embodiment of the present invention, a health functional food for preventing or alleviating alcoholic liver disease, which includes β-glucan as an active ingredient, is provided.

According to yet another exemplary embodiment of the present invention, the use of β-glucan in a pharmaceutical composition for relieving a hangover is provided.

According to yet another exemplary embodiment of the present invention, the use of β-glucan in a pharmaceutical composition for preventing or treating alcoholic liver disease is provided.

According to yet another exemplary embodiment of the present invention, the use of β-glucan in a health functional food for relieving a hangover is provided.

According to yet another exemplary embodiment of the present invention, the use of β-glucan in a health functional food for preventing or alleviating alcoholic liver disease is provided.

According to yet another exemplary embodiment of the present invention, a method of relieving a hangover, which includes administering β-glucan to a subject, is provided.

According to yet another exemplary embodiment of the present invention, a method of treating alcoholic liver disease, which includes administering β-glucan to a subject, is provided.

The present invention relates to a composition for relieving a hangover or a composition for preventing, alleviating or treating alcoholic liver disease, which includes β-glucan as an active ingredient. The composition can relieve a hangover through the breakdown of alcohol or acetaldehyde, and suppress side effects caused by a hangover, that is, a body weight gain, hepatotoxicity and an increase in blood cholesterol level. Therefore, by using the composition, it is expected to relieve a hangover in a safe manner to a human body without a side effect caused by a hangover.

In addition, the composition according to the present invention has an effect of preventing, alleviating or treating alcoholic liver disease.

DETAILED DESCRIPTION OF THE INVENTION

The inventors had tried to relieve a hangover in a safe manner to a human body without a side effect caused by a hangover, and thus confirmed that, when β-glucan was treated, alcohol or acetaldehyde can be effectively broken down, and a body weight gain, hepatotoxicity and an increase in blood cholesterol level can be suppressed, and thus the present invention was completed.

Hereinafter, the present invention will be described in detail.

Pharmaceutical Composition for Relieving Hangover/Preventing or Treating Alcoholic Liver Disease The present invention provides a pharmaceutical composition for relieving a hangover, which includes β-glucan as an active ingredient.

The pharmaceutical composition for relieving a hangover according to the present invention includes β-glucan as an active ingredient.

The pharmaceutical composition is effective in relieving a hangover relieves a hangover, and such hangover relieving effect may be confirmed by measuring ADH and ALDH activities or blood alcohol and acetaldehyde concentrations.

In addition, the pharmaceutical composition for relieving a hangover is for suppressing side effects which are caused by a hangover or accompany alcohol consumption, and specifically, the side effects may be due to a body weight gain, or hepatotoxicity or an increase in blood cholesterol level. More specifically, the body weight gain may be determined by measuring a body weight and blood triglyceride levels, and the hepatotoxicity may be determined by measuring a liver weight or analyzing GOT/AST levels and γ-GPT/ALT levels.

In addition, the present invention provides a pharmaceutical composition for preventing or treating alcoholic liver disease, which includes β-glucan as an active ingredient.

The pharmaceutical composition for preventing or treating alcoholic liver disease is for preventing or treating alcoholic liver disease, and here, alcoholic liver disease refers to one or more diseases including hepatitis, cirrhosis and fatty liver, which are caused by liver injury induced by alcohol, but the present invention is not limited thereto. The effect of preventing or treating alcoholic liver disease may be determined by measuring the weight of an alcohol-induced liver, or analyzing GOT/AST levels and γ-GPT/ALT levels.

The β-glucan is provided to primarily break down alcohol or acetaldehyde, secondarily suppress side effects caused by a hangover, that is, a body weight gain, hepatotoxicity and an increase in blood cholesterol level, or prevent, alleviate or treat alcoholic liver disease. The β-glucan preferably has the structure of β-(1,6)-branched (1,3)-glucan, but the present invention is not limited thereto. The β-glucan may be derived from microbial cells, yeast cells or mushroom mycelia, and more specifically, isolated from *Schizophyllum commune* or a culture thereof, but the present invention is not limited thereto.

To isolate the β-glucan form *Schizophyllum commune*, *Schizophyllum commune* mycelia may be obtained from a culture obtained by liquid culture. More specifically, as disclosed in Korean Patent No. 10-0892355 or 10-0909857, *Schizophyllum commune* was cultured, and β-glucan is preferably isolated and obtained from the culture thereof, but the present invention is not limited thereto.

The β-glucan is contained preferably at 0.001 to 50 wt %, and more preferably, 0.005 to 20 wt % with respect to the total weight of the pharmaceutical composition, but the present invention is not limited thereto.

The pharmaceutical composition according to the present invention may be used in the formulation of an oral preparation such as powder, granules, tablets, capsules, suspensions, emulsions or syrups, a preparation for external use, a suppository and a sterile injectable solution according to a conventional method, and for formulation, suitable carriers, excipients or diluents conventionally used in the preparation of a pharmaceutical composition may be included.

As the carriers, excipients or diluents, various compound or mixtures including lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate and mineral oil may be used.

In preparation, generally used diluents or excipients such as a filler, a thickening agent, a binder, a wetting agent, a disintegrating agent and a surfactant may be used.

Solid preparations for oral administration may be prepared by mixing at least one excipient selected from starch, calcium carbonate, sucrose, lactose and gelatin with the β-glucan. In addition to simple excipients, lubricants such as magnesium stearate and talc may also be used.

Liquid preparations for oral administration may be suspensions, liquids for internal use, emulsions or syrups, and may include, in addition to simple diluents frequently used, various excipients, for example, a wetting agent, a sweetening agent, a flavoring agent, a preservative, etc.

Preparations for parenteral administration include a sterile aqueous solution, water, a non-aqueous vehicle, a suspending agent, an emulsifier, a lyophilizing agent, and a suppository. As a non-aqueous vehicle or a suspending agent, propylene glycol, polyethylene glycol, a vegetable oil such as olive oil, or an injectable ester such as ethyl oleate may be used. As a base material for suppositories, Witepsol®, Macrogol, Tween 61, cacao butter, laurin butter or glycerol gelatin may be used.

A preferred dose of the pharmaceutical composition according to the present invention may be determined according to a patient's condition, body weight, the severity of a disease, a drug type, an administration route and an administration duration, and properly selected by one of ordinary skill in the art. However, for a preferred effect, the pharmaceutical composition is preferably administered 0.0001 μg/kg to 400 mg/kg, and more preferably, 0.001 to 200 mg/kg per day. The pharmaceutical composition may be administered once a day or several times by dividing the daily dose. However, the above-mentioned dose does not limit the scope of the present invention.

The pharmaceutical composition according to the present invention may be administered to mammals such as rats, mice, livestock or humans in various routes. All modes of administration, for example, oral, parenteral, rectal, intravenous, intramuscular, subcutaneous, intrauterine, and intracerebroventricular injections may be administered.

Heath Functional Food for Relieving Hangover

The present invention provides health functional food for relieving a hangover, which contains β-glucan as an active ingredient.

The health functional food for relieving a hangover according to the present invention contains β-glucan as an active ingredient, and the β-glucan is the same as described above.

In addition, the present invention provides health functional food for preventing or alleviating alcoholic liver disease, which includes β-glucan as an active ingredient.

The health functional food for preventing or alleviating alcoholic liver disease according to the present invention contains β-glucan as an active ingredient, and the β-glucan is the same as described above.

In the health functional food according to the present invention, when the β-glucan is used as an additive for the health functional food, it may be added by itself or used with other food or food ingredients, and may be properly used according to a conventional method. The mixed amount of the active ingredient may be properly determined according to the purpose of use, for example, prevention, health or treatment.

The health functional food may be used in any formulation such as a common food or beverage form as well as powder, granules, pills, tablets or capsules.

The type of food is not particularly limited, and examples of food to which the material is added may be meat, sausages, bread, chocolate, candies, snacks, confectionery, pizza, ramen, other noodles, gum, dairy product including ice creams, various types of soup, beverages, tea, drinks, alcoholic beverages and vitamin complexes, and in the common sense, all types of food may be included.

Generally, in preparation of food or a beverage, the β-glucan may be added at 15 parts by weight or less, and preferably, 10 parts by weight or less, with respect to 100 parts by weight of the raw materials. However, in the case of long-term consumption for health and hygiene or health control, the amount may be in the range or less, and since the present invention uses a natural substance, it has no problem in terms of safety, and thus can be used in an amount above the range.

A beverage among the health functional food according to the present invention may contain additional ingredients such as various flavoring agents or natural carbohydrates. The above-mentioned natural carbohydrates may include monosaccharides such as glucose and fructose, disaccharides such as maltose and sucrose, polysaccharides such as dextrin and cyclodextrin, and sugar alcohols such as xylitol, sorbitol and erythritol. Sweetening agents may include natural sweetening agents such as thaumatin and *Stevia* extracts, and synthetic sweetening agents such as saccharin and aspartame. The proportion of the natural carbohydrate may be approximately 0.01 to 0.04 g, and preferably, approximately 0.02 to 0.03 g per 100 mL of the beverage according to the present invention.

In addition to the above ingredients, the health functional food according to the present invention may contain various nutrients, vitamins, electrolytes, flavors, colorants, pectic acid and a salt thereof, alginic acid and a salt thereof, organic acids, protective colloidal thickening agents, pH regulators, stabilizers, preservatives, glycerin, and a carbonating agent used in an alcohol or carbonated drink. These ingredients may be used independently or in combination. Generally, the proportion of the additive may be, but is not limited to, 0.01 to 0.1 part by weight with respect to 100 parts by weight of the health functional food of the present invention.

Further, the present invention provides the use of β-glucan in a pharmaceutical composition for relieving a hangover.

In addition, the present invention provides the use of β-glucan in a pharmaceutical composition for preventing or treating alcoholic liver disease.

Moreover, the present invention provides the use of β-glucan in a health functional food for relieving a hangover.

In addition, the present invention provides the use of β-glucan in a health functional food for preventing or alleviating alcoholic liver disease.

In addition, the present invention provides a method of relieving a hangover, which includes administering β-glucan to a subject.

In addition, the present invention provides a method of treating alcoholic liver disease, which includes administering β-glucan to a subject.

The term "subject" used herein refers to a target in need of treatment, and more specifically, a mammal such as a human or a non-human primate, a mouse, a rat, a dog, a cat, a horse, or a cow.

As described above, the present invention relates to a composition for relieving a hangover or a composition for preventing or treating alcoholic liver disease, which includes β-glucan as an active ingredient, and the composition can break down alcohol or acetaldehyde to relieve a hangover, and suppress side effects caused by a hangover, that is, a body weight gain, hepatotoxicity and an increase in blood cholesterol level. Accordingly, according to the composition, it is expected that a hangover can be relieved in a safe manner to a human body without a side effect caused by a hangover.

In addition, the composition according to the present invention has an effect of preventing, alleviating or treating alcoholic liver disease.

Hereinafter, to help in understanding the present invention, exemplary examples will be suggested. However, the following examples are merely provided to more easily understand the present invention, and not to limit the present invention.

EXAMPLES

Example 1: Confirmation of Alcohol Breakdown Effect According to β-Glucan Administration in Short-Term Alcohol Consumption (Animal Testing)

Six-week-old wild-type C57BL/6 mice were purchased, acclimated for 3 days and then raised. Specifically, the mice were divided into a total of four groups of five mice, as shown in Table 1, 0.2 mL of 20% ethanol (EtOH) was orally administered to each of Experimental Group 1 and Comparative Experimental Group 1. Thirty minutes after the administration, 0.2 mL of *Schizophyllum commune*-derived β-glucan (SPG with the structure of β-(1,6)-branched (1,3)-glucan; Manufacturer: Quegen Biotech Co., Ltd.; Conc.=1.6 mg/mL) was orally administered to Experimental Group 1, and a phosphate buffer solution (PBS) instead of SPG was orally administered to Comparative Experimental Group 1. Meanwhile, SPG and PBS were orally administered to Comparative Experimental Groups 2 and 3 without alcohol administration, respectively.

TABLE 1

| | Concentration of administered drug | Dose |
|---|---|---|
| Experimental Group 1 | 20% EtOH + SPG 1.6 mg/mL | 0.2 mL each |
| Comparative Experimental Group 1 | 20% EtOH + PBS | 0.2 mL each |
| Comparative Experimental Group 2 | SPG 1.6 mg/mL | 0.2 mL each |
| Comparative Experimental Group 3 | PBS | 0.2 mL |

It was confirmed whether animal models who consumed alcohol for a short time exhibit effects of increasing ADH and NAD-dependent ALDH activities and decreasing blood alcohol and acetaldehyde levels when β-glucan was orally administered.

Figure 1:
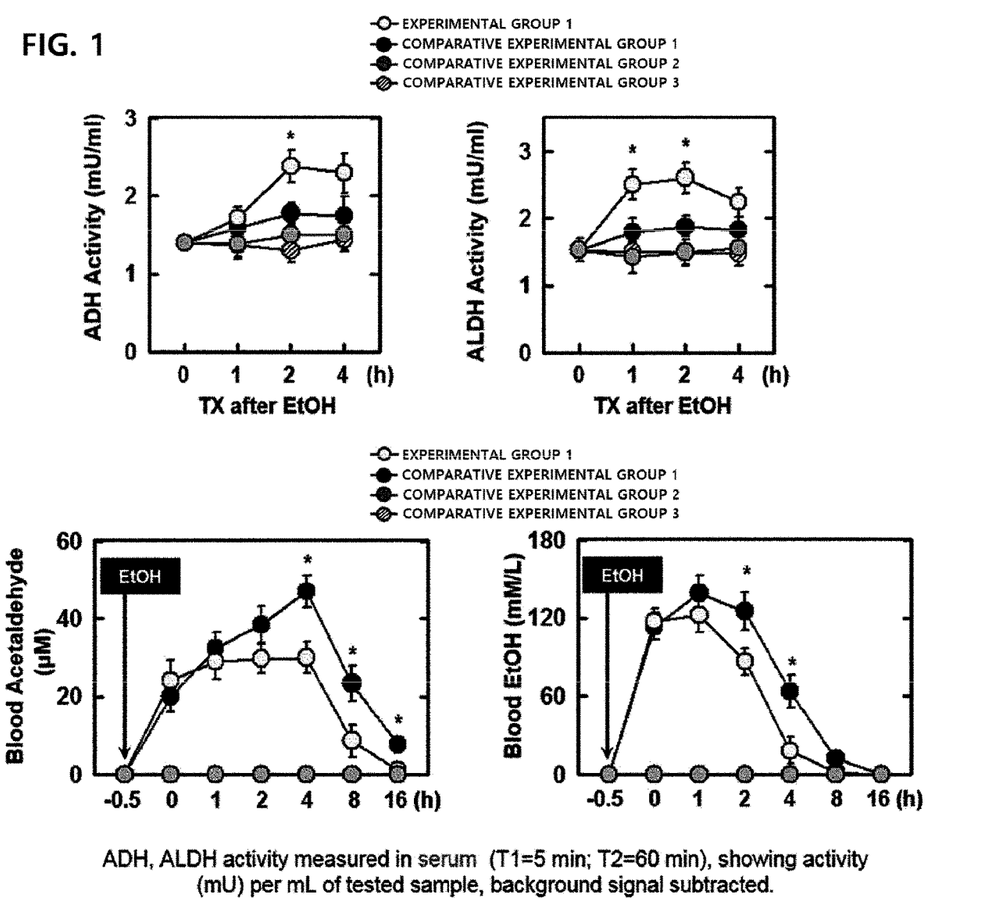
FIG. 1 is a set of graphs comparing the results of measuring ADH and ALDH activities, and blood alcohol and acetaldehyde concentrations by collecting blood at 1, 2 and 4 hours after β-glucan or PBS is administered to Experimental Group 1 and Comparative Experimental Groups 1 to 3, and isolating serum from each group.

Specifically, ADH and ALDH activities, and blood alcohol and acetaldehyde levels were measured by collecting blood at 1, 2 and 4 hours after β-glucan or PBS was administered to each of Experimental Group 1 and Comparative Experimental Groups 1 to 3 and isolating serum, and the result is shown in FIG. 1.

As shown in FIG. 1, in Experimental Group 1 consuming alcohol for a short time and then treated with β-glucan via an oral route, compared to Comparative Experimental Group 1, it was confirmed that ALD and ALDH activities greatly increase. However, in Comparative Experimental Group 2 not consuming alcohol for a short time and then treated with β-glucan via an oral route, the increase in the activities of such enzymes was not confirmed.

In addition, compared to Comparative Experimental Group 1, in Experimental Group 1, it was confirmed that both of the blood alcohol and acetaldehyde levels greatly decrease.

Example 2: Confirmation of Alcohol Breakdown According to β-Glucan Administration in Long-Term Alcohol Consumption (Animal Testing)

Six-week-old wild-type C57BL/6 mice were purchased, and raised after acclimation for 3 days. Specifically, after the mice were divided into a total of four groups of five mice as shown in Table 1, 0.2 mL of 20% ethanol (EtOH) was orally administered to each of Experimental Group 1 and Comparative Experimental Group 1, after 30 minutes, 0.2 mL of *Schizophyllum commune*-derived β-glucan (SPG with the structure of β-(1,6)-branched (1,3)-glucan; Manufacturer: Quegen Biotech Co., Ltd.; Conc.=1.6 mg/mL) was orally administered to Experimental Group 1, and a phosphate buffer solution (PBS) instead of SPG was orally administered to Comparative Experimental Group 1. Such a process was continuously repeated four times every hour. Meanwhile, SPG and PBS were orally administered to Comparative Experimental Group 3 and 4 four times at the same time interval without alcohol administration, respectively.

TABLE 2

|  | Concentration of administered drug | Dose | Number of alcohol consumption |
|---|---|---|---|
| Experimental Group 1 | 20% EtOH + SPG 1.6 mg/mL | 0.2 mL each | 4 times |
| Comparative Experimental Group 1 | 20% EtOH + PBS | 0.2 mL each | 4 times |

TABLE 2-continued

|  | Concentration of administered drug | Dose | Number of alcohol consumption |
|---|---|---|---|
| Comparative Experimental Group 2 | SPG 1.6 mg/mL | 0.2 ml | 0 time |
| Comparative Experimental Group 3 | PBS | 0.2 mi | 0 time |

It was confirmed whether animal models who consumed alcohol for long time exhibit effects of decreasing blood alcohol and blood acetaldehyde levels by orally administering β-glucan.

Figure 2:
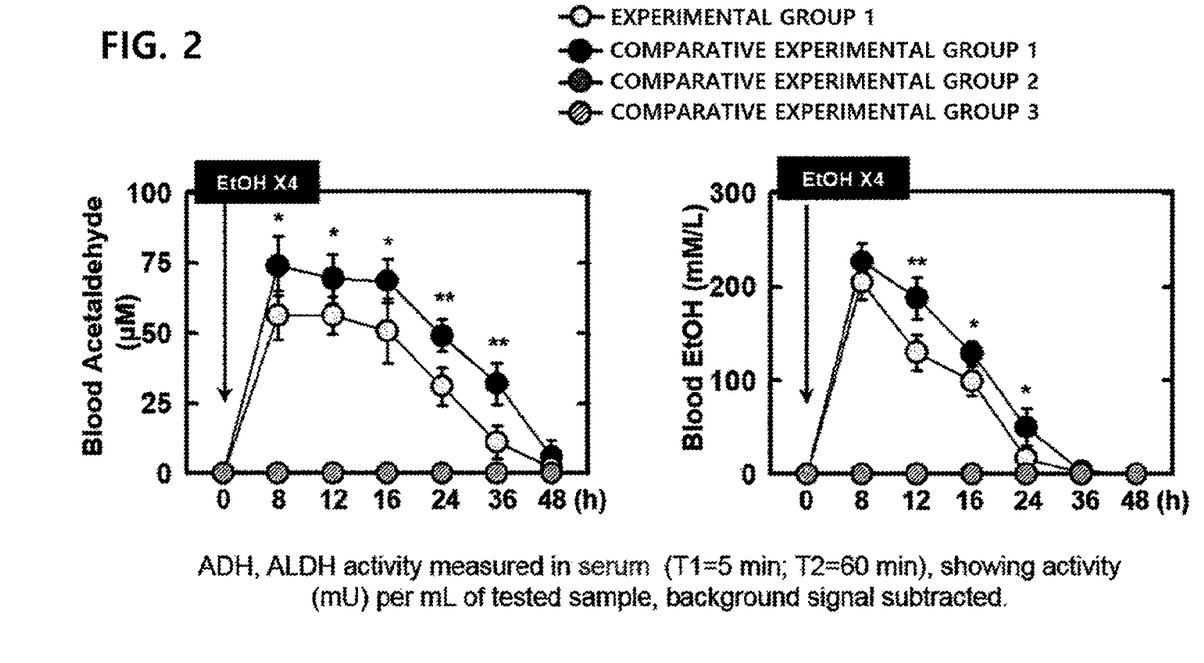
FIG. 2 is a set of graphs comparing the results of measuring blood alcohol and acetaldehyde concentrations by collecting blood six times hourly from 5 hours after β-glucan or PBS is administered to Experimental Group 1 and Comparative Experimental Groups 1 to 3, and isolating serum from each group.

Specifically, blood alcohol and acetaldehyde levels were measured by collecting blood 6 times hourly from 5 hours after β-glucan or PBS was administered to Experimental Group 1 and Comparative Experimental Groups 1 to 3 and isolating serum, and the result is shown in FIG. 2.

As shown in FIG. 2, in Experimental Group 1 consuming alcohol for long time and then treated with β-glucan via an oral route, compared to Comparative Experimental Group 1, it was confirmed that all of the blood alcohol and blood acetaldehyde levels greatly decrease.

Example 3: Confirmation of Inhibitory Effect on Side Effects Caused by Hangover or Therapeutic Effect on Alcoholic Liver Disease According to β-Glucan Administration in Long-Term Alcohol Consumption (Animal Testing)

Six-week-old wild-type C57BL/6 mice were purchased, and raised after acclimation for 3 days. Specifically, after the mice were divided into a total of four groups of five mice, as shown in Table 1, 0.2 mL of 20% ethanol (EtOH) was orally administered to each of Experimental Group 1 and Comparative Experimental Group 1, after 30 minutes, 0.2 mL of *Schizophyllum commune*-derived β-glucan (SPG with the structure of β-(1,6)-branched (1,3)-glucan; Manufacturer: Quegen Biotech Co., Ltd.; Conc.=1.6 mg/mL) was orally administered to Experimental Group 1, and a phosphate buffer solution (PBS) instead of SPG was orally administered to Comparative Experimental Group 1. Such a process was continuously repeated four times every hour. Meanwhile, SPG and PBS were orally administered to Comparative Experimental Group 3 and 4 four times at the same time interval without alcohol administration, respectively. The administration was repeated for 6 weeks five times a week.

TABLE 3

|  | Concentration of administered drug | Dose | Number of administration per week | Total administration time |
|---|---|---|---|---|
| Experimental Group 1 | 20% EtOH + SPG 1.6 mg/mL | 0.2 mL each | 5 times | 6 weeks |
| Comparative Experimental Group 1 | 20% EtOH + PBS | 0.2 mL each | 5 times | 6 weeks |
| Comparative Experimental Group 2 | SPG 1.6 mg/mL | 0.2 ml | 5 times | 6 weeks |
| Comparative Experimental Group 3 | PBS | 0.2 ml | 5 times | 6 weeks |

It was confirmed whether animal models who consumed alcohol for long time exhibit an inhibitory effect on side effects caused by a hangover and a therapeutic effect on alcoholic liver disease according to the oral administration of β-glucan.

Figure 3:
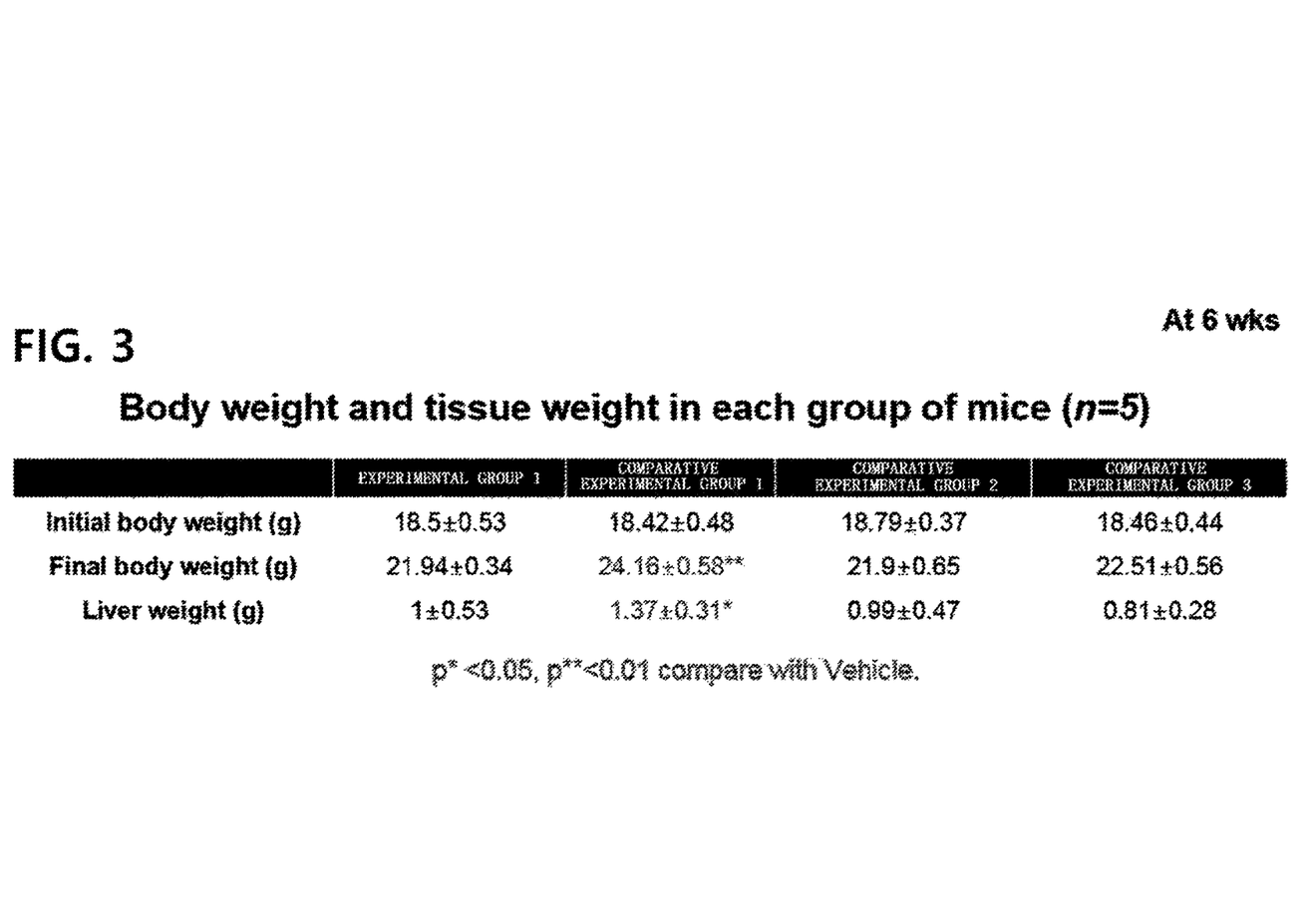
FIG. 3 is a table comparing the results of measuring body weights and liver tissue weights after the sacrifice of mice 6 weeks after β-glucan or PBS is administered to Experimental Group 1 and Comparative Experimental Groups 1 to 3.
Figure 4:
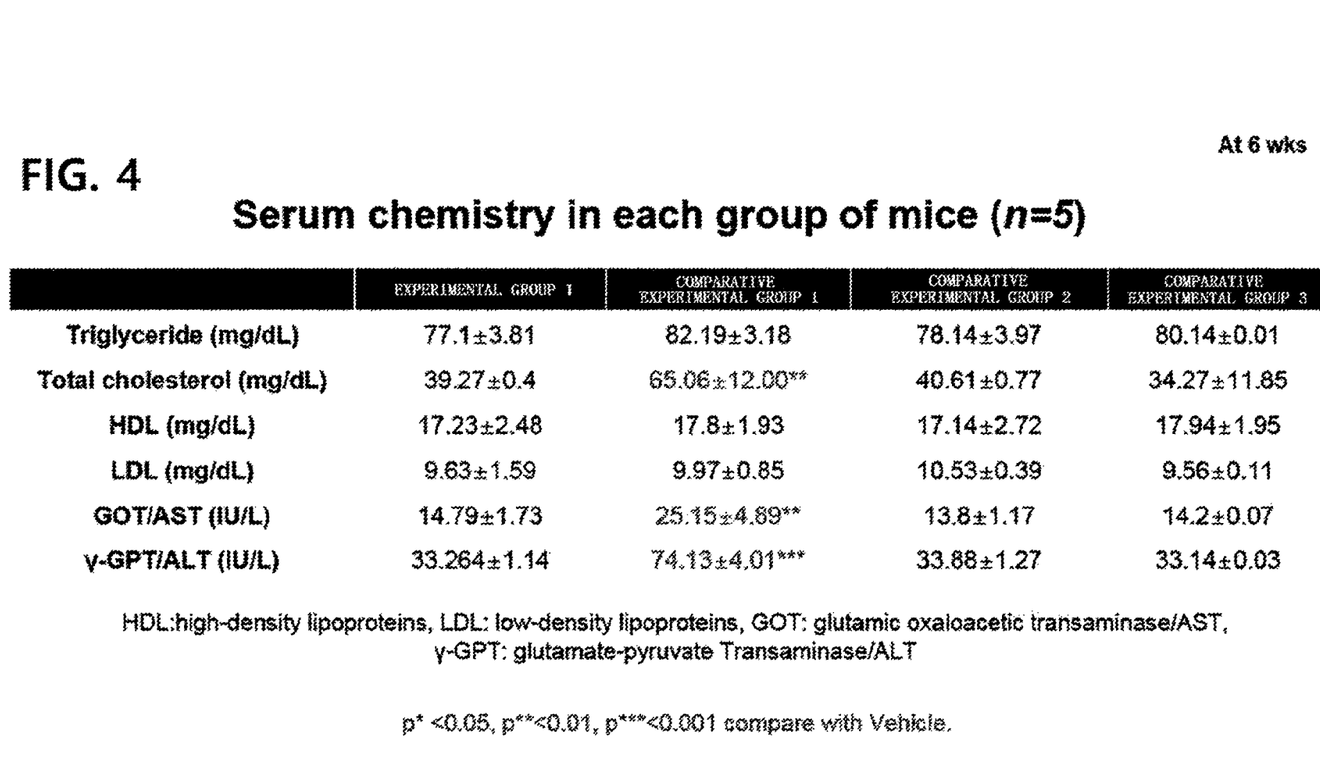
FIG. 4 is a table comparing the results of analyzing sera after the sacrifice of mice 6 weeks after β-glucan or PBS is administered to Experimental Group 1 and Comparative Experimental Groups 1 to 3.

Specifically, the mice of Experimental Group 1 and Comparative Experimental Groups 1 to 3 were sacrificed 6 weeks after the administration of β-glucan or PBS began, and measured in body weight and liver tissue weight. The result is shown in FIG. 3. In addition, serum analysis was performed, and the result is shown in FIG. 4.

As shown in FIG. 3, it was confirmed that Experimental Group 1 that consumed alcohol for long time and then was treated with β-glucan via an oral route, compared to Comparative Experimental Group 1, was greatly decreased in body weight and liver tissue weight. In addition, as shown in FIG. 4, it is confirmed that, in Experimental Group 1, compared to in Comparative Experimental Group 1, a blood triglyceride level decreased, a blood cholesterol level greatly decreased, and a blood GOT/AST level and a γ-GPT/ALT level greatly decreased.

Hereinafter, preparation examples for compositions containing the compound of the present invention will be described. The present invention is merely provided to describe the examples in detail, but not limited thereto.

Preparation Example 1: Preparation of Powder

β-glucan, 20 mg

Lactose hydrate, 100 mg

Tale, 10 mg

A powder was prepared by mixing the ingredients and filling an airtight pouch with the mixture.

Preparation Example 2: Preparation of Tablet

β-glucan, 10 mg
Corn starch, 100 mg
Lactose hydrate, 100 mg
Magnesium stearate, 2 mg A tablet was prepared by mixing the ingredients and tableting the mixture according to a conventional method of preparing a tablet.

Preparation Example 3: Preparation of Capsule

β-glucan, 10 mg
Microcrystalline cellulose, 3 mg
Lactose hydrate, 14.8 mg
Magnesium stearate, 0.2 mg A capsule was prepared by mixing the ingredients and filling a gelatin capsule with the mixture according to a conventional method of preparing a capsule.

Preparation Example 4: Preparation of Injection

β-glucan, 10 mg
Mannitol, 180 mg
Sterile distilled water for injection, 2974 mg
Sodium hydrogen phosphate, 26 mg An injection was prepared by mixing the above-described ingredients to contain them per ampoule (2 mL) according to a conventional method of preparing an injection.

Preparation Example 5: Preparation of Liquid

β-glucan, 10 mg
Isomerized glucose syrup, 10 g
Mannitol, 5 g
Distilled water, q. s.
Lemon flavor, q. s.

A liquid was prepared by dissolving the above-described ingredients in distilled water according to a conventional preparation method, adding an appropriate amount of lemon flavor, adding distilled water to adjust a total volume to 100 mL, and then filling a sterile brown bottle with the resulting mixture.

Preparation Example 6: Preparation of Health Functional Food

β-glucan, 10 mg
Vitamin mixture, q.s.
Vitamin A acetate, 70 μg
Vitamin E, 1.0 mg
Vitamin $B_1$, 0.13 mg
Vitamin $B_2$, 0.15 mg
Vitamin $B_6$, 0.5 mg
Vitamin $B_{12}$, 0.2 μg
Vitamin C, 10 mg
Biotin, 10 μg
Nicotinic acid amide, 1.7 mg
Folic acid, 50 μg
Calcium pantothenate, 0.5 mg
Mineral mixture, q. s.
Ferrous sulfate, 1.75 mg
Zinc oxide, 0.82 mg
Magnesium carbonate, 25.3 mg
Potassium monophosphate, 15 mg
Potassium diphosphate, 55 mg
Potassium citrate, 90 mg
Calcium carbonate, 100 mg
Magnesium chloride, 24.8 mg The mixture of vitamins and minerals was prepared by mixing relatively suitable ingredients for a health functional food in a preferred composition ratio, but the mixing ratio may be arbitrarily modified. A granule was prepared by mixing the above-described ingredients according to a conventional method of preparing a health functional food, and can be used in preparation of a health functional food according to a conventional method.

Preparation Example 7: Preparation of Health Drink

β-glucan, 10 mg
Vitamin C, 15 g
Vitamin E (powder), 100 g
Iron lactate, 19.75 g
Zinc oxide, 3.5 g
Nicotinic acid amide, 3.5 g
Vitamin A, 0.2 g
Vitamin $B_1$, 0.25 g
Vitamin $B_2$, 0.3 g
Distilled water, q. s.

A health drink composition of the present invention was prepared by mixing the above-described ingredients according to a conventional method of preparing a health drink, heating the mixture while stirring for 1 hour at 85° C. filtering the resulting solution, putting the filtered solution into a sterilized 2 L container and sealing the container, sterilizing the solution, and then storing the sterilized product in a refrigerator.

Although the composition was prepared by mixing ingredients relatively suitable for beverage preference, a mixing ratio may be arbitrarily modified according to a regional or ethnic preference such as a class of people or countries that consume the composition, or the purpose of use thereof.

It would be understood by those of ordinary skill in the art that the above descriptions of the present invention are exemplary, and the example embodiments disclosed herein can be easily modified into other specific forms without changing the technical spirit or essential features of the present invention. Therefore, it should be interpreted that the example embodiments described above are exemplary in all aspects, and are not limitative.

The invention claimed is:

1. A method for relieving a hangover, comprising orally administering an effective amount of R-(1,6)-branched (1,3)-glucan isolated from *Schizophyllum commune* or a culture thereof to a subject in need thereof, wherein the effective amount is obtained when administration of the β-(1,6)-branched (1,3)-glucan suppresses a side effect caused by the hangover, wherein the side effect is body weight gain and/or increased blood triglyceride levels.

2. The method of claim 1, wherein the β-(1,6)-branched (1,3)-glucan is contained in a composition at 0.001 to 50 wt % with respect to the total weight of the composition.

* * * * *